(12) United States Patent
Maloney et al.

(10) Patent No.: US 9,125,919 B2
(45) Date of Patent: Sep. 8, 2015

(54) ACNE TREATMENT POWDER FOUNDATION

(75) Inventors: John D. Maloney, Salisbury, NC (US); Katherine Natalie Barger, Davidson, NC (US)

(73) Assignee: EI LLC, Raleigh, NC (US)

( * ) Notice: Subject to any disclaimer, the term of this patent is extended or adjusted under 35 U.S.C. 154(b) by 386 days.

(21) Appl. No.: 12/639,851

(22) Filed: Dec. 16, 2009

(65) Prior Publication Data

US 2010/0183528 A1 Jul. 22, 2010

Related U.S. Application Data

(60) Provisional application No. 61/138,436, filed on Dec. 17, 2008.

(51) Int. Cl.

| A61P 17/10 | (2006.01) |
|---|---|
| A61K 8/368 | (2006.01) |
| A61Q 1/00 | (2006.01) |
| A61Q 17/04 | (2006.01) |
| A61K 31/60 | (2006.01) |
| A61K 8/27 | (2006.01) |
| A61K 8/29 | (2006.01) |
| A61K 8/35 | (2006.01) |
| A61K 8/81 | (2006.01) |
| A61K 8/97 | (2006.01) |
| A61K 31/12 | (2006.01) |
| A61K 31/315 | (2006.01) |
| A61K 33/04 | (2006.01) |
| A61K 33/24 | (2006.01) |
| A61K 33/30 | (2006.01) |
| A61K 45/06 | (2006.01) |
| A61Q 1/12 | (2006.01) |

(52) U.S. Cl.
CPC . *A61K 31/60* (2013.01); *A61K 8/27* (2013.01); *A61K 8/29* (2013.01); *A61K 8/35* (2013.01); *A61K 8/368* (2013.01); *A61K 8/8152* (2013.01); *A61K 8/97* (2013.01); *A61K 31/12* (2013.01); *A61K 31/315* (2013.01); *A61K 33/04* (2013.01); *A61K 33/24* (2013.01); *A61K 33/30* (2013.01); *A61K 45/06* (2013.01); *A61Q 1/12* (2013.01); *A61K 2800/56* (2013.01)

(58) Field of Classification Search
None
See application file for complete search history.

(56) References Cited

U.S. PATENT DOCUMENTS

| 5,449,519 | A |   | 9/1995 | Wolf et al. |   |
|---|---|---|---|---|---|
| 5,919,467 | A | * | 7/1999 | Jenkins et al. | 424/401 |
| 6,235,297 | B1 |   | 5/2001 | Antonelli et al. |   |
| 6,331,305 | B1 |   | 12/2001 | Sang |   |
| 6,387,995 | B1 |   | 5/2002 | Sojka |   |
| 6,416,748 | B1 |   | 7/2002 | Candau et al. |   |
| 6,475,500 | B2 |   | 11/2002 | Vatter et al. |   |
| 6,491,953 | B1 |   | 12/2002 | Sojka et al. |   |
| 6,524,598 | B2 |   | 2/2003 | Sunkel et al. |   |
| 6,599,513 | B2 |   | 7/2003 | Deckers et al. |   |
| 6,696,049 | B2 |   | 2/2004 | Vatter et al. |   |
| 6,831,191 | B2 |   | 12/2004 | Chaudhuri |   |
| 7,115,282 | B2 |   | 10/2006 | Shefer et al. |   |
| 7,166,273 | B2 |   | 1/2007 | Chaudhuri |   |
| 7,208,460 | B2 |   | 4/2007 | Shefer et al. |   |
| 7,247,323 | B2 |   | 7/2007 | George et al. |   |
| 7,250,174 | B2 |   | 7/2007 | Lee et al. |   |
| 7,297,678 | B2 |   | 11/2007 | Kumar et al. |   |
| 7,304,177 | B2 |   | 12/2007 | Kleiman et al. |   |
| 7,329,719 | B2 |   | 2/2008 | Pavlin |   |
| 2004/0219124 | A1 |   | 11/2004 | Gupta |   |
| 2004/0234633 | A1 | * | 11/2004 | Kim et al. | 424/769 |
| 2005/0002996 | A1 | * | 1/2005 | Sojka | 424/445 |
| 2005/0031658 | A1 | * | 2/2005 | Girier Dufournier et al. | 424/401 |
| 2005/0129759 | A1 | * | 6/2005 | Sojka | 424/469 |
| 2005/0226830 | A1 | * | 10/2005 | Fang | 424/63 |
| 2005/0249720 | A1 | * | 11/2005 | Perez | 424/94.65 |
| 2005/0265934 | A1 | * | 12/2005 | Schumacher et al. | 424/59 |
| 2006/0198800 | A1 |   | 9/2006 | Dilallo et al. |   |
| 2007/0071978 | A1 | * | 3/2007 | Sojka et al. | 428/402.2 |
| 2007/0258919 | A1 |   | 11/2007 | Angel et al. |   |
| 2008/0070875 | A1 |   | 3/2008 | Majewski et al. |   |
| 2008/0138293 | A1 | * | 6/2008 | Tamarkin et al. | 424/45 |
| 2008/0181920 | A1 | * | 7/2008 | Buerger et al. | 424/401 |
| 2008/0193393 | A1 |   | 8/2008 | Dayan |   |
| 2009/0215723 | A1 | * | 8/2009 | Le | 514/63 |
| 2009/0246156 | A1 | * | 10/2009 | Kunin | 424/60 |

FOREIGN PATENT DOCUMENTS

| CN | 1539433 A | 10/2004 |
|---|---|---|
| KR | 1020030005485 A | 1/2003 |
| WO | WO9504537 A1 | 2/1995 |
| WO | WO0073374 A1 | 7/2000 |

OTHER PUBLICATIONS

Houston Healthcare, "Nonsteroidal Anti-Inflamatory Drugs", http://www.hhc.org/HealthTopics.aspx?chunkid=21396&lang=English&db=hlt#p8, accessed Jan. 24, 2014.*
Mintel GNPD, "XP-002676188 Glowtion to Go Moisturizer", Accessed online at GNPD Database (www.gnpd.com), Jun. 1999, pp. 1-2.
Mintel GNPD, "XP-002676203 Healing Powder", Accessed online at GNPD database (www. gnpd.com) Feb. 2008, pp. 1-2.

* cited by examiner

*Primary Examiner* — Bethany Barham
*Assistant Examiner* — Melissa Javier
(74) *Attorney, Agent, or Firm* — Hultquist, PLLC; Steven J. Hultquist; Mary B. Grant

(57) ABSTRACT

Dry powder foundation formulations that include a sustained-release salicylic acid composition, an effective, buffering amount of one or more salicylate ions, and one or more of zinc and titanium oxides, and pigments or colorants, are disclosed. The formulations provide both acne treatment and prevention, and sunblock protection. The formulation can also include other sunblocking or sunscreen agents to prevent photoaging and sunburn, such as avobenzone, and 3-benzophenone, and other cosmetically-acceptable active agents and excipients.

19 Claims, No Drawings

ACNE TREATMENT POWDER FOUNDATION

CROSS-REFERENCE TO RELATED APPLICATION

This is a U.S. non-provisional of U.S. Provisional Patent Application No. 61/138,436 filed on Dec. 17, 2008. The disclosure of the foregoing application is hereby incorporated herein by reference in its respective entirety, for all purposes, and the priority of such application is hereby claimed under the provisions of 35 USC 119.

BACKGROUND OF THE INVENTION

Acne is the most common skin disorder in the US, and although this condition is generally associated with puberty, it is not confined to adolescence and can persist well into adulthood. The acne condition is a complex one, impacted by a number of intrinsic and extrinsic factors, and, as such, must be treated with a multifaceted approach. Treatment should address overproduction of sebum, hyperkeratinization, overgrowth of P. acnes, and the ultimate blockage and irritation of the pilosebaceous follicle. Extrinsic factors, which exacerbate the acne condition, involve exfoliation via harsh abrasives or mechanical scrubbing, UV exposure, and some topical and oral substances.

Salicylic acid is a relatively mild beta-hydroxy acid, which is proven effective at correcting abnormal desquamation, the natural shedding of the outermost stratum corneum cells. Its treatment benefits extend beyond that of the acne condition to include psoriasis, keratoses, and ichthyoses. By penetrating into the follicle, salicylic acid encourages the sloughing of dead skin cells and other cellular debris and, ultimately, clears blockages. Further benefits of its exfoliating action are improvements in skin texture and hyperpigmentation.

While there are a wide variety of products on the market containing salicylic acid for treating the acne condition, most are in the forms of lotions, creams, and liquids, including liquid foundation makeup. Incorporation of salicylic acid into color foundations is advantageous, as it helps to clear current breakouts while concealing them. Furthermore, continued use will help to prevent future breakouts. Loose powder foundations are currently enjoying much popularity, as they impart a lightweight, natural feel on the skin while providing great coverage, long wearability, oil absorption, and diffuse the appearance of blemishes and other skin imperfections. Providing a loose powder foundation with acne treatment benefits would represent an improvement over an already popular product type.

However, the presence of free salicylic acid may serve to irritate the skin. Accordingly, it would be advantageous to provide a loose powder foundation that provides the benefits of salicylic acid, while minimizing the degree of skin irritation. The present invention provides such a foundation.

SUMMARY OF THE INVENTION

The present invention relates to a cosmetic composition, in the form of a dry powder foundation, that includes a sustained-release salicylic acid composition, an effective, buffering amount of one or more salicylate ions, and one or more of zinc and titanium oxides. The composition can also include other cosmetically-acceptable actives and excipients found in dry powder foundations. The composition can be used as a foundation that provides both acne treatment and prevention and sunblock protection.

Because the composition provides salicylic acid in the form of a sustained-release composition, the salicylic acid remains effective for an extended period of time. Poly Pore 450SA, a polymeric formulation including salicylic acid in an allyl methacrylate crosspolymer, is a representative polymeric sustained-release form of salicylic acid, though other sustained-release formulations can also be used. Further, as anti-acne additives, the formulation includes one or more salicylates, ideally isolated as an extract from willow bark and/or aspen bark. In addition to the salicylic acid and one or more salicylates, the formulation can also include other anti-acne agents, including sulfur, benzoyl peroxide, and resorcinol.

In addition to normal excipients found in dry powder foundations, the formulation includes zinc oxide and/or titanium dioxide as sunblocking agents. The formulation can also include other sunblocking or sunscreen agents to prevent photoaging and sunburn, such as avobenzone, and 3-benzophenone.

The foundation formulation typically also includes colorants/pigments, for example, inorganic colorants/pigments, one example of which is a blend of iron oxide, bismuth oxychloride, and mica.

In one embodiment, the composition further includes one or more additional components, such as zinc gluconate, Active Powder Purity LS 9695, and pearl powder, such as PPP-100 pearl powder.

In one aspect of this embodiment, the formulation has the following ingredients, in the ranges of weight percentages provided below in Table 1.

TABLE 1

Representative Formulation Ranges

| Ingredient | Range % w/w |
|---|---|
| Iron Oxide, Bismuth Oxychloride & Mica blend | 40-75 |
| Titanium Dioxide | 5-40 |
| Zinc Oxide | 5-35 |
| Poly-Pore 450SA | 0.10-12.00 |
| Salicylic Acid & Allyl Methacrylates Crosspolymer | |
| ABS White Willow Bark Extract Powder | 0.10-10.00 |
| Salix Nigra (Willow) Bark Extract | |
| Phytocide Aspen Bark Extract Powder | 0.10-10.00 |
| Populus Tremuloides (Aspen) Bark Extract | |
| Givobio GZn | 0.10-10.00 |
| Zinc Gluconate | |
| Active Powder Purity LS 9695 | 0.10-10.00 |
| Exfoliance Bamboo | 0.10-10.00 |
| Bambusa Arundinacea Stem Powder | |
| PPP-100 Pearl Powder | 0.10-10.00 |
| Pearl Powder | |

The foundation formulations combine the benefits of acne treatment and UV protection with lightweight coverage. The foundation formulations combat acne by reducing & regulating sebum production, providing gentle exfoliation, destroying P. acnes and other harmful microbes, soothing irritation and inflammation, and restoring barrier function. The incorporation of sunscreens also helps to improve acne, as UV exposure is known to exacerbate the condition.

In some embodiments, the formulation can have a sun protection factor (SPF) of 15 or more. The formulation can help heal blemishes and prevent future breakouts, clear blockages, and help improve skin texture and hyperpigmentation remaining after breakouts. The salicylic acid/salicylate combination reduces and absorbs surface sebum, provides gentle exfoliation and stimulates natural exfoliation, and provides anti-microbial activity. The formulation can provide antioxidant activity, soothe skin and mitigate irritation, provides a modern, natural look, provide excellent coverage and wearability, and diffuse the look of blemishes and uneven pigmentation The present invention will be better understood with reference to the following detailed description.

DETAILED DESCRIPTION

A dry powder foundation formulation is disclosed. The dry powder foundation formulation includes conventional foundation ingredients, as well as sunblocking agents and anti-acne additives. The formulation provides controlled release of salicylic acid, and includes extracts containing one or more salicylate salts.

Definitions

The following definitions will be useful in understanding the invention described herein.

In this disclosure, the term "salicylate ion" includes naturally-occurring and man-made salicylate ions, and specifically includes extracts of willow bark and aspen bark, which include natural salicylates. The term "effective, buffering amount" refers to an amount of salicylate ion capable of neutralizing, at least in part, the acidic nature of the salicylic acid. For example, the presence of 10 percent or more of the molar amount of salicylates, relative to salicylic acid, can be effective.

The terms "cosmetic" or "cosmetic products" or "cosmetic compositions" as used herein, mean (i) articles intended to be rubbed into, applied with a brush, or otherwise applied to the face of a human for cleaning, beautifying, promoting attractiveness, or altering the appearance, and (ii) articles intended for use as a component of any such articles, e.g., sun screening compositions, medicinal compositions, and the like.

I. Formulation Components

The foundation includes conventional dry powder formulation components, anti-acne agents, and sunblocking agents, and can also include a variety of other agents designed to provide beneficial treatments to the skin of the user.

The acne treatment powder foundation is a multipurpose product, combining the benefits of acne treatment and UV protection with lightweight yet superior coverage compared to traditional loose powder foundations. The foundation combats acne by reducing & regulating sebum production, providing gentle exfoliation, destroying P. acnes and other harmful microbes, soothing irritation and inflammation, and restoring barrier function. Incorporation of sunscreens also helps improve acne, as UV exposure is known to exacerbate the condition.

Like conventional dry powder foundations, the foundation formulation described herein also includes colorants/pigments. In one embodiment, the composition further includes one or more additional components, such as zinc gluconate, Active Powder Purity LS 9695, and pearl powder, such as PPP-100 pearl powder. Additional active agents, as well as non-active agents (excipients) can be present. The various active agents and optional components are described in more detail below.

Acne Treatment

The anti-acne additives include a combination of a sustained-release salicyclic acid composition, and salicylates, either in the form of a natural extract or as a pure compound. Examples of extracts that include salicylates include willow bark and aspen bark. The amount of the sustained-release salicylic acid composition, by weight percent, typically ranges from between about 0.10 to about 12.00, which provides between about 0.05 to about 6.00 free salicylic acid. The amount of the salicylates, by weight percent, typically ranges from between about 0.10 to about 10.00, which can be present in the form of an extract of a natural product that includes salicylates, such as willow bark and aspen bark. When in the form of an extract, the extract itself is typically present in a range of between about 0.055 to about 5.50 free salicylic acid.

Salicylic acid is a mild keratolytic agent, which promotes desquamation. The acne treatment powder foundation formulation described herein uses an extended-release salicylic acid delivery system. Representative extended-release/sustained-release delivery systems include, but are not limited to, Poly Pore 450 SA, MultiSal™ Salicylic Acid 10, MultiSal™ SAL 20, MultiSal™ Salicylic Acid 30, Biogenic Salicylic Acid, and Lipo CD-SA. This slow, sustained release of the active allows for long-lasting availability and helps to minimize irritation.

Poly Pore 450 SA is a polymeric formulation including salicylic acid in an allyl methacrylate crosspolymer. MultiSal™ consists of solid hydrophobic nanospheres encapsulated in a water or pH sensitive microsphere. Biogenic Salicylic Acid is a proprietary material which encapsulates salicylic acid, and has a roughly 25% concentration of salicylic acid. Lipo CD-SA is a proprietary material comprising 5% Salicylic acid in encapsulated powder form.

To supplement the action of salicylic acid, natural salicylates, White Willow Bark and Aspen Bark Extracts, are added to enhance the anti-acne activity by providing additional exfoliation and antimicrobial action. White Willow Bark has been shown to accelerate cell renewal more effectively compared to free salicylic acid, while Aspen Bark works as an ideal preservative, inhibiting growth of molds, yeast, and a wide array of bacteria.

Salicylic acid is a keratolytic agent; promotes desquamation, clears blockages, helps prevent new lesions, & improves skin texture and hyperpigmentation after breakouts. The sustained release form of salicylic acid helps to minimize irritation and provide long-lasting availability of the active ingredient. Irritation is mitigated by minimizing the concentration of salicylic acid contacting the skin at any given moment. The presence of salicylates also helps reduce the acidity of the salicylic acid, by providing a buffer. That is, when an acid (in this case, salicylic acid) and its conjugate base (in this case, salicylates) are present in a formulation, each buffers the other, according to the well-known Henderson-Hasselbach equation (pH=pKa+log (concentration of acid/concentration of base).

Any cosmetically-acceptable salt of salicylic acid (i.e., salicylate) can be used in the formulations described herein. Representative salts include, but are not limited to, salts with cations of ammonium, sodium, potassium, magnesium, calcium, strontium, barium, aluminum, iron, zinc, bismuth and organic amines. A salt with at least one of these cations is preferable. More preferable is a sodium, potassium, magnesium or zinc salt, still more preferable is a sodium, potassium or zinc salt, and particularly preferable is a sodium salt.

The salicylic acid and salicylates can be used in concentrations from about 0.05% to about 12.0% by weight, where the amount of free salicylic acid ranges from about 0.10 to about 6.0 by weight.

Other representative anti-acne agents that can be used, in addition to the salicylic acid and salicylates, include sulfur, benzoyl peroxide, resorcinol, and resorcinol monoacetate. When present, sulfur is typically in an amount of between 0.1 and 10.0% w/w; benzoyl peroxide is typically in an amount of between 0.5 and 5.0% w/w, resorcinol is typically in an amount of between 0.1 and 2.0% w/w, and resorcinol monoacetate is typically in an amount of between 0.1 and 3.0% w/w.

Additional Optional Anti-Acne Agents

In addition to the salicylic acid, salicylates, and the other anti-acne agents listed above, other anti-acne agents can be included in the dry powder foundation described herein. Non-limiting examples of useful anti-acne actives include the keratolytics such as salicylic acid (o-hydroxybenzoic acid), derivatives of salicylic acid such as 5-octanoyl salicylic acid and 4 methoxysalicylic acid; retinoids such as retinoic acid and its derivatives (e.g., cis and trans); sulfur-containing D and L amino acids and their derivatives and salts, particularly their N-acetyl derivatives, a preferred example of which is N-acetyl-L-cysteine; lipoic acid; sebostats such as flavonoids and bioflavonoids; bile salts such as scymnol sulfate and its derivatives, deoxycholate, and cholate; abietic acid; adapalene; allantoin; aloe extracts; arbietic acid and its salts; aryl-2,4 dioxo oxazolidine derivatives; ASEBIOL (available from Laboratories Serobiologiques, located in Somerville, N.J.); azaleic acid; barberry extracts; bearberry extracts; belamcanda chinensis; benzoquinolinones; benzoyl peroxide; berberine; BIODERMINE (available from Sederma, located in Brooklyn, N.Y.); bioflavinoids; bisabolol; S-carboxymethyl cysteine; carrot extracts; cassin oil; clove extracts; citral; citronellal; climazole; Completech MBAC-OS (available from Lipo); CREMOGEN M82 (available from Dragoco, located in Totowa, N.J.); cucumber extracts; dehydroacetic acid and its salts; dehydroeplandersterone salicylate; dichlorophenyl imidazoldioxolan which is commercially available as COMPLETECH MBAC-OS (from Lipo, located in Paterson, N.J.); DL valine and its esters; DMDM hydantoin; Epicutin TT (available from CLR); erythromycin; escinol; ethyl hexyl monoglyceryl ether; ethyl 2-hydroxy undecanoate; farnesol; farnesol acetate; geranoil; glabridin; gluconic acid; gluconolactone; glyceryl monocaprate; glycolic acid; grapefruit seed extract; gugu lipid; Hederagenin (available from Maruzen); hesperitin; hinokitol; hops extract; hydrogenated rosin; 10 hydroxy decanoic acid; ichtyhol; interleukin 1 alpha antagonists; iodo-2-propynyl butyl carbamate; Kapilarine (available from Greentech); ketoconazole; lactic acid; lemon grass oil; Lichochalcone LR15 (available from Maruzen); linoleic acid; LIPACIDE C8CO (available from Seppic, located in Paris, France); lovastatin; 4 methoxysalicylic acid; metronidazole; minocycline; mukurossi; neem seed oil; vitamin $B_3$ compounds (such as niacinamide and nicotinic acid); nisin; 5-octanoly salicylic acid; octopirox; panthenol; 1-pentadecanol; peonia extract; peppermint extract; phelladendron extract; 2-phenyl-benzothiophene derivatives; phloretin; PHLOROGINE (available from Secma); phosphatidyl choline; proteolytic enzymes; quercetin; red sandalwood extract; resorcinol; rosemary extract; rutin; sage extract; salicin; salicylic acid; skull cap extract; siber hegner extract; siberian saxifrage extract; silicol; sodium lauryl sulfate; sodium sulfoacetamide; Sophora Extract (available from Maruzen); sorbic acid; sulfur; sunder vati extract; tea tree oil; tetracyline; tetra hydroabietic acid; thyme extract; tioxolone; tocopherol; trehalose 6-undecylenoate; 3 tridecene-2-ol; triclosan; tropolone; UNI-TRIENOL T27 (available from Unichem, located in Gouda, Netherlands); vitamin $D_3$ and its analogs; white thyme oil; willow bark extract; wogonin; Ylang Ylang; zinc glycerolate; zinc linoleate; zinc oxide; zinc pyrithione; zinc sulfate and mixtures thereof.

UV Protection

Sunscreen and/or sunblocking agents are present in the dry powder foundation described herein. The term "sunscreen agent" as used herein defines ultraviolet ray-blocking compounds exhibiting absorption within the wavelength region between about 290 and about 400 nm.

The formulation includes, as sunblocking agents, one or more of zinc oxide and titanium dioxide, and, most preferably, a combination of these two agents. The range of these ingredients in the formulations is typically between about 8.10 and about 35.00 weight percent for titanium dioxide, and between about 10 and about 25.65 weight percent for zinc oxide.

Zinc oxide and titanium dioxide are mineral pigments often used for photoprotection, as they are opaque to both UVA and UVB radiation. Although both provide opacity to UV light, titanium dioxide provides 3 to 4 times better coverage and photoprotection. Titanium dioxide is a physical sunscreen providing covering power and UV protection. Zinc oxide is a physical sunscreen that provides covering power and UV protection; reduces sebum production, may promote wound healing, and has powerful antioxidant activity. Zinc oxide also provides additional benefits beyond UV protection. Zinc is a component of at least 70 metalloenzymes and is also needed in protein, DNA, and RNA synthesis. In addition, it is a cofactor for Superoxide Dismutase (SOD), an enzyme providing crucial antioxidant activity and alleviating oxidative stress in cells. Zinc oxide is classified as a Category 1 skin protectant, provides antimicrobial activity, and is thought to be implicated in reducing sebum production and promoting wound healing.

Utilizing a combination of these two compounds will provide ample UV protection, while also supplementing acne treatment and improving skin condition.

Ideally, the particle sizes of these agents are in the micron size or less. Microparticulate (also known as microfine) zinc oxide and titanium dioxide are particulate sunscreen ingredients that absorb broad-spectrum ultraviolet (UV) irradiation.

Additional Optional Sunscreen Actives/UV Absorbers

In addition to titanium dioxide and/or zinc oxide, other organic sunscreens can also be used. Also, UV absorbers, such as 3-benzophenone and avobenzone can be present in the formulation. When present, 3-benzophenone is typically present in a concentration of between about 0.1 and about 10 weight percent, and avobenzone is typically present in a concentration of between about 0.1 and about 5 weight percent.

Other representative sunscreens and sunblocking agents include iron oxide and polymer particles such as those of polyethylene, polymethylmethacrylates and polyamides A wide variety of conventional sunscreening agents are suitable for use in the present invention as described in Segarin et al., at Chapter VIII, Pages 189 et seq., "Cosmetics Science and Technology", the disclosure of which is incorporated herein by reference.

Sunscreens are typically classified into five groups based upon their chemical structure: para-amino benzoates; salicylates; cinnamates; benzophenones; and miscellaneous chemicals including menthyl anthranilate and digalloyl trioleate. Salicylates are present in the composition as anti-acne agents, and thus serve a dual role as a sunscreen.

Specific suitable sunscreening agents include, for example: p-aminobenzoic acid, its salts and derivatives, anthranilates, salicylates, cinnamic acid derivatives, dihydroxycinnamic acid derivatives, trihydroxycinnamic acid derivatives, hydrocarbons, dibenzalacetone and benzalacetophenone, naphthosulfonates, dihydroxy-naphthoic acid and its salts, o- and p-hydroxy-biphenyldisulfonates, coumarin derivatives, diazoles, quinine salts, quinoline derivatives, hydroxy or methoxy substituted benzophenones, uric and vilouric acids, tannic acid and its derivatives, hydroquinone, benzophenones, and the like.

Also useful herein are sunscreening actives. A wide variety of sunscreening agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991.

Non-limiting examples of sunscreens which are useful in the compositions of the present invention are those selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomethyl salicylate, octyl salicylate, 4,4'-methoxy-t-butyldibenzoylmethane, 4-isopropyl dibenzoylmethane, 3-benzylidene camphor, 3-(4-methylbenzylidene)camphor, titanium dioxide, zinc oxide, silica, iron oxide, and mixtures thereof. Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991; these two references are incorporated by reference herein in their entirety. Still other useful sunscreens include aminobenzoic acid (PABA), benzylidene camphor, butyl methoxy dibenzoyl methane, diethanolamine p-methoxycinnamate, dioxybenzone, ethyl dihydroxypropyl (PABA), glyceryl aminobenzoate, homomethyl salicylate, isopropyl dibenzoyl methane, lawsone and dihydroxyacetone, menthyl anthranilate, methyl anthranilate, methyl benzylidene camphor, octocrylene, octyl dimethyl (PABA), octyl methoxycinnamate, oxybenzone, 2-phenylbenzimidazole-5-sulfonic acid, red petrolatum, sulisobenzone, titanium dioxide, triethanolamine salicylate, zinc oxide, and mixtures thereof. Especially preferred examples of these sunscreens include those selected from the group consisting of 4-N,N-(2-ethylhexyl)methylaminobenzoic acid ester of 2,4-dihydroxybenzophenone, 4-N,N-(2-ethylhexyl)methylaminobenzoic acid ester with 4-hydroxydibenzoylmethane, 4-N,N-(2-ethylhexyl)-methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy)dibenzoylmethane, and mixtures thereof.

The exact amounts of sunscreens which can be used will vary depending upon the sunscreen chosen and the desired Sun Protection Factor (SPF) to be achieved. SPF is a commonly used measure of photoprotection of a sunscreen against erythema. See Federal Register, Vol. 43, No. 166, pp. 38206-38269, Aug. 25, 1978, which is incorporated herein by reference in its entirety.

SPF of the Resulting Formulations

It is believed that the formulations can provide an SPF of around 15, particularly when rubbed into the skin rather than simply being dusted onto the skin. The SPF can be measured, for example, using a Labsphere UV-1000S UV transmittance analyzer, which is commonly used to obtain in vitro SPF data on cosmetic products.

Optional Additional Components

The dry powder foundation formulations described herein can include, in addition to excipients, the salicylic acid and salicylates, and the zinc oxide and/or titanium dioxide, other active agents. These agents, and their relative weight percentages in the formulation, are listed in Table 2 below. These components can help to boost treatment of the acne condition, or can have additional beneficial properties.

One example of an additional component is Active® Powder Purity LS 9695 by Cognis Corporation. Active® Powder Purity (also referred to herein as AP Purity) is composed of B vitamins, panthenol, biotin, and niacinamide, and various extracts to regulate sebum, inhibit lipogenesis, and provide an anti-inflammatory effect. In a 4 week clinical study evaluating the active fraction of Active® Powder Purity, the results showed a 16.6% decrease in the number of active sebaceous glands and a 21.6% decrease in seborrheic flux after treatment. Furthermore, in vitro testing on human fibroblasts confirmed that this active fraction reduced excess sebum secretion via inhibition of 5α-reductase enzyme, and this effect increased with duration and concentration of treatment. 5α-Reductase converts testosterone to dihydrotestosterone (DHT) in sebaceous cells. DHT stimulates sebum secretion, and, thus, inhibiting its production will reduce sebum levels.

Active® Powder Purity includes a significant amount of water-based active specifically designed to control sebum regulation and inhibit lipogenesis. Because of the encapsulation process, AP Purity can be formulated into all anhydrous systems such as loose and pressed powders, hot pour sticks and silicone-based serums. It is designed to treat oily, troubled and/or blemished skin, and is perfectly suited for acne preparations.

Although the exact amounts of each active are not listed here, the components include water, lauryl methacylate/glycol dimethacrylate crosspolymer, dicaprylyl ether, niacinamide, yeast extract, *Aesculus Hippocastanum* (Horse Chestnut) seed extract, titanium dioxide, algae extract, ammonium glycyrrhizate, panthenol, zinc gluconate, caffeine, xanthan gum, polyglyceryl-2-dipolyhydroxystearate, and biotin Zinc gluconate is another optional component, and further supports sebum regulation and antimicrobial activity. Both Zinc and gluconate ions are intimately involved in skin metabolism and provide a soothing, anti-inflammatory effect.

Pearl powder can also be used. Pearl powder includes many beneficial ingredients, such as amino acids, some of which cannot be synthesized in the human body, and bio-available minerals, including calcium, magnesium, and selenium. Used since ancient times, particularly in Chinese medicines, it is believed to enhance moisturization, exfoliation, skin repair, and UV protection. Pearl Powder has been used for helping to treat blemishes, pigmentation disorders, and restoring proper barrier function. It has been shown to reduce Transepidermal Water Loss (TEWL), the amount of water passively diffusing through the stratum corneum and a direct correlation to barrier intactness.

Bamboo extract can also be used. Bamboo extract offers gentle exfoliation by removing dead cells and debris from the skin surface. A clinical study evaluating the ingredient's efficacy showed a significant exfoliating effect after only 14 days of use.

Pigments/Colorants

Other additives that can be added to the present invention include dispersed inorganics (colorants) and pigments. Such dispersed inorganics and pigments include, but are not limited to, fumed silica, microfine pigments, particularly oxides and silicates, e.g. iron oxide, particularly coated iron oxides, and/or titanium dioxide, and ceramic materials such as boron nitride, or other solid components such as barium sulfate, bismuth oxychloride, and mica.

Representative Formulation

In one embodiment, the formulation includes Iron Oxides, Bismuth Oxychloride, & Mica as colorants, titanium dioxide and zinc oxide as physical sunscreens, Poly-Pore 450SA (salicylic acid and allyl methacrylate crosspolymer) as a salicylic acid sustained-release formulation, ABS White Willow Bark Extract Powder and PhytoCide Aspen Bark Extract Powder as sources of salicylate, zinc gluconate, Active® Powder Purity LS 9695, Bambusa Arundinacea Stem Powder, PPP-100 Pearl Powder, and one or more of dicaprylyl ether, niacinamide, yeast extract, *Aesculus Hippocastanum* (Horse Chestnut) seed extract, algae extract, ammonium glycyrrhizate, panthenol, caffeine, xanthan gum, polyglyceryl-2 dipolyhydroxystearate, and biotin.

Additional Optional Active Agents

The controlled release system described herein includes salicylic acid as a primary active agent, naturally-occurring or purified salicylates, and zinc oxide and/or titanium dioxide as sunblocking agents, in the form of a dry powder foundation.

The foundation can also include, in addition to these agents, other cosmetic, dermatological, and pharmaceutical active agents, including, but are not limited to: anti-oxidants; free radical scavengers; depigmentation agents; reflectants; antimicrobial (e.g., antibacterial) agents; allergy inhibitors; anti-aging agents; anti-wrinkling agents, antiseptics; analgesics; anti-inflammatory agents; fresheners; healing agents; anti infectives; inflammation inhibitors; vasoconstrictors; vasodilators; wound healing promoters; peptides, polypeptides and proteins; skin lightening agents; antifungals; counterirritants; make-up preparations; vitamins; amino acids and their derivatives; herbal extracts; flavoids; sensory markers (i.e., cooling agents, heating agents, etc.); skin conditioners; chelating agents; cell turnover enhancers; nourishing agents; moisture absorbers; sebum absorbers and the like; skin penetration enhancers; and other active ingredients.

Fragrances and Sensory Markers

The formulation described herein also provides synchronizing the release of the sensory markers such as fragrances, flavors, cooling agents, such as menthol derivatives, and heating agents, such as capsaicin. The release of the sensory markers can be used to convey to the consumer the product performance, provide long lasting odor or flavor perception, and signal that a new application of the product is needed.

Conventional fragrance ingredients and perfume ingredients can be used in the release system of the present invention. Selection of any perfume component, or amount of perfume, is based on functional and aesthetic considerations. Examples of usable fragrance and flavor compounds discussed hereinafter, along with their odor characters, and their physical and chemical properties, are given in "Perfume and Flavor Chemicals (Aroma Chemicals)", Steffen Arctander, published by the author, 1969, and in "Common Fragrance and flavor Materials-Preparation, Properties and Uses", Kurt Bauer and Dorotea Garbe, published by VCH Verlagsgesellschaft mbH, 1985, incorporated herein by reference.

Botanical extracts are oak bark extract, walnut extract, tincture of arnica, hamamelis extract, ribwort extract, pansy extract, thyme or sage extract; for the treatment of damaged or injured skin, for example, St. John's wort tincture, cone flowers tincture, chamomile flowers extract, or calendula flowers tincture; and for the care of exhausted and damaged skin, for example, birch leaves extract, nettle extract, coldsfoot extract, comfrey tincture, horsetail extract, or aloe vera extract. Vegetable preparations may also be released from the film layer for the intradermal treatment of diseases, for example, extracts of horse chestnut and butcher's broom in case of vein diseases, or extracts and tinctures of arnica, calendula, and capsicum in case of contusions, distortions, or haemorrhages. Vegetable preparations in the system, according to the present invention may also be used in transdermal therapy, for example, ginseng extract in case of geriatric complaints; valerian tincture, extracts of melissa and hop to cause a sedative effect in case of superexcitation, sleep disturbances, and stress; extracts of kola and tea to achieve a stimulative effect; or hawthorn extract to stabilize the circulatory system.

Preservatives

Preservatives can desirably be incorporated into the dry powder foundation described herein to protect against the growth of potentially harmful microorganisms. While microorganisms tend to grow in the aqueous phase, microorganisms can also reside in the anhydrous or oil phase. As such, preservatives which have solubility in both water and oil are preferably employed in the present compositions. Suitable preservatives for compositions of the present invention are alkyl esters of para-hydroxybenzoic acid. Other preservatives, which can be used include hydantoin derivatives, propionate salts, and a variety of quaternary ammonium compounds.

Appropriate preservatives can be selected to satisfy the preservative challenge test and to provide product stability. Particularly preferred preservatives are methylparaben, imidazolidinyl urea, sodium dehydroacetate, propylparaben, trisodium ethylenediamine tetraacetate (EDTA), and benzyl alcohol. The preservative can be selected based on the consideration of possible incompatibilities between the preservative and other ingredients in the release system.

Preservatives are preferably employed in amounts ranging from about 0.01% to about 2% by weight of the composition.

Vitamins

Various vitamins can be included in the dry powder foundation described herein. For example, vitamin A and derivatives thereof, vitamin B2, biotin, pantothenic acid, vitamin K, vitamin D, vitamin E and mixtures thereof can be used.

Antimicrobial and Antifungal Actives

Antimicrobial and antifungal actives can be effective to prevent the proliferation and growth of bacteria and fungi and can be used in the dry powder foundation described herein. Non-limiting examples of antimicrobial and antifungal actives include beta-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate, zinc pyrithione; clotrimazole; alantolactone; isoalantolactone; alkanet extract (alaninin); anise; arnica extract (helenalin acetate and 11,13 dihydrohelenalin); Aspidium extract (phloro, lucinol containing extract); barberry extract (berberine chloride); bay sweet extract; bayberry bark extract (myricitrin); benzalkonium chloride; benzethonium chloride; benzoic acid and its salts; benzoin; benzyl alcohol; blessed thistle; bletilla tuber; bloodroot; bois de rose oil; burdock; butyl paraben; cade oil; CAE (available from Ajinomoto, located in Teaneck, N.J.); cajeput oil; Cangzhu; capsicum frutescens extract; caraway oil; cascarilla bark (sold under the tradename ESSENTIAL OIL); cedarleaf oil; chamomille; chaparral; chlorhexidine gluconate; chlorophenesin; chlorxylenol; cinnamon oil; citronella oil; clove oil; Crinipan AD (available from Climbazole); 2,3-dihydro-farnesol; dehydroacetic acid and its salts; dill seed oil; DOWICIL 200 (available from Dow Chemical, located in Midland, Mich.); echinacea; elenolic acid; epimedium; ethyl paraben; Fo-Ti; galbanum; garden bumet; GERMALL 115 and GERMALL II (available from ISP-Sutton Labs, located in Wayne, N.J.); German chamomile oil; giant knotweed; GLYDANT (available from Lonza, located in Fairlawn, N.J.); GLYDANT PLUS (available from Lonza); grapefruit seed oil; 1,6 hexanediol; hexamidine diisethionate; hinokitiol; honey; honeysuckle flower; hops; immortelle; iodopropynl butyl carbamide (available from Lonza); isobutyl paraben; isopropyl paraben; JM ACTICARE (available from Microbial Systems International, located in Nottingham, NG); juniper berries; KATHON CG (available from Rohm and Haas, located in Philadelphia, Pa.); kojic acid; labdanum; lavender; lemon balm oil; lemon grass; methyl paraben; mint; mume; mustard; myrrh; neem seed oil; ortho phenyl phenol; olive leaf extract (available from Bio Botanica); parsley; patchouly oil; peony root; 1,2 pentandiol; PHENONIP (available from Nipa Labs, located in Wilmington, Del.); phenoxyethanol; phytosphingosine; pine needle oil; PLANSERVATIVE (available from Campo Research); propyl paraben; purslane; quillaira; rhubarb; rose geranium oil; rosemary; sage; salicylic acid; sassafras; savory; sichuan lovage; sodium meta bisulfite; sodium sulfite; SOPHOLIANCE (available from Soliance, located in Compiegne, France); sorbic acid and its salts; sphingosine; stevia; storax; sucrose esters; tarmic acid; tea; tea tree oil (cajeput oil); thyme; triclosan; triclocarban; tropolone; turpentine; umbelliferone (antifungal); yucca; and mixtures thereof.

Anti-Inflammatory Agents

Anti-inflammatories can be included in dry powder foundation described herein to enhance photoprotection benefits, particularly from UVA.

Suitable steroidal anti-inflammatories include hydrocortisone; non-steroidal anti-inflammatories such as oxicans, salicylates, acetic acid derivatives, fenamates, propionic acid derivatives, pyrazoles, substituted phenyl compounds, 2-naphthyl containing compounds, and natural anti-inflammatories such as aloe vera. Examples of anti-inflammatories are described in U.S. Pat. No. 5,487,884, the entire contents of which are incorporated herein by reference.

Anti-Wrinkle, Anti-Skin Atrophy and Skin Repair Actives

Anti-wrinkle, anti-skin atrophy and skin repair actives can be effective in replenishing or rejuvenating the epidermal layer and can be included in dry powder foundation described herein. These actives generally provide these desirable skin care benefits by promoting or maintaining the natural process of desquamation.

Nonlimiting examples of anti-wrinkle and anti-skin atrophy actives include vitamin B3 compounds (such as niacinamide and nicotinic acid), salicylic acid and derivatives thereof (such as 5-octanoyl salicylic acid, heptyloxy 4 salicylic acid, and 4-methoxy salicylic acid); sulfur-containing D and L amino acids and their derivatives and salts, particularly the N-acetyl derivatives, a preferred example of which is N-acetyl-L-cysteine; thiols, e.g. ethane thiol; hydroxy acids, phytic acid, lipoic acid; lysophosphatidic acid; skin peel agents (e.g., phenol and the like); Actein 27-Deoxyactein Cimicifugoside (available from Cirnigoside); adapalene; ademethionine; adenosine; aletris extract; alkyl glutathione esters; alkoxyalkoxy alkoxyn benzoic and derivatives; aloe derived lectins; amino propane phosphoric acid; 3-aminopropyl dihydrogen phosphate; Amadorine (available from Barnet Products); anise extracts; AOSINE (available from Secma); arginine amino benzoate; ASC III (available from E. Merck, located in Darmstadt, Germany); ascorbic acid; ascorbyl palmitate; asiatic acid; asiaticosides; ARLAMOL GEO™ (available from ICI, located in Wilmington, Del.); azaleic acid; benzoic acid derivatives; bertholletia extracts; betulinic acid; BIOCHANIN A AND BIOPEPTIDE CL (available from Sederma, located in Brooklyn, N.Y.); BIOPEPTIDE EL (available from Sederma); biotin; blackberry bark extract; blackberry lily extracts; black cohosh extract; blue cohesh extract; butanoyl betulinic acid; carboxymethyl 1,3 beta glucan; catecholamines; chalcones; citric acid esters; chaste tree extract; clover extracts; coumestrol; CPC Peptide (available from Barnet Products); daidzein; dang gui extract; darutoside; debromo laurinterol; 1-decanoyl-glycero-phosphonic acid; dehydrocholesterol; dehydrodicreosol; dehydrodieugenol; dehydroepiandersterone; DERMOLECTINE (available from Sederma); dehydroascorbic acid; dehydroepiandersterone sulfate; dianethole; hydroxy benzoic acid; 2,4 dihydroxybenzoic acid; diglycol guanidine succinate; diosgenin; disodium ascorbyl phosphate; dodecanedioic acid; Ederline (available from Seporga); Enderline (available from Laboratories Seporga); equol; eriodictyol; estrogen and its derivatives; ETF (available from Laboratories Seporga); ethocyn; ELESERYL SH (available from Laboratories Serobiologiques, located in Somerville, N.J.); ENDONUCLEINE (available from Laboratories Serobiologiques); ergosterol; eythrobic acid; fennel extract; fenugreek seed extract; FIBRASTIL (available from Sederma); FIBROSTIMULINES S and P (available from Sederma); FIRMOGEN LS 8445 (available from Laboratories Serobiologiques); formononetin; forsythia fruit extract; gallic acid esters; gamma amino butyric acid; GATULINE RC (available from Gattlefosse, located in Priest, France); genistein; genisteine; genistic acid; gentisyl alcohol; gingko bilboa extracts; ginseng extracts; ginsenoside (RO, R61, R62, R63, Rc, RD, RE, RF, RF-2, RG-I, RG-2); gluco pyranosyl-L-ascorbate; glutathione and its esters; glycitein; hesperitin; hexahydro curcumin; HMG-coenzyme A reductase inhibitors; hops extracts; 11 hydroxy undecanoic acid; 10 hydroxy decanoic acid; 25-hydroxycholesterol; 7-hydroxylated sterols; hydroxyethyl isostearyloxy isopropanolamine; hydroxy-tetra methyl piperidinyloxy; hypotaurine; ibukijakou extract; isoflavone SG 10 (available from Barnet Products); kinetin; kohki extract; L-2-OXO-thiazolidine-4-carboxylic acid esters; lactate dehydrogenase inhibitors; 1-lauryl, -lyso-phosphatidyl choline; lectins; lichochalcone LF15 (available from Maruzen); licorice extracts; lignan; lumisterol; lupenes; luteolin; lysophosphitidic acid; magnesium ascorbyl phosphate; margin; melatonin; melibiose; metalloproteinase inhibitors; methoprene; methoprenic acid; mevalonic acid; MPC COMPLEX (available from CLR); N methyl serine; N methyl taurine; N, NI-Ws (lactyl) cysteamin; naringenin; neotigogenin; o-desmethylangoiensin; oat beta glucan; oleanolic acid; pantethine; phenylalanine; photoanethone; piperidine; placental extracts; pratensein; pregnenolone; pregnenolone acetate; pregnenolone succinate; premarin; quillaic acid; raloxifene; REPAIR FACTOR 1 and REPAIR FACTOR FCP (both available from Sederma); retinoates (esters of $C2._{20}$ alcohols); retinyl glucuronate; retinyl linoleate; S-carboxymethyl cysteine; SEANAMINE FP (available from Laboratories Serobiologiques); sodium ascorbyl phosphate; soya extracts; spleen extracts; tachysterol; taurine; tazarotene; tempol; thymulen; thymus extracts; thyroid hormones; tigogenin; tocopheryl retinoate; toxifolin; traumatic acid; tricholine citrate; trifoside; uracil derivatives; ursolic acid; vitamin D3 and its analogs; vitamin K; vitex extract; yam extract; yamogenin; zeatin; and mixtures thereof.

Skin Barrier Repair Actives

Skin barrier repair actives are those skin care actives which can help repair and replenish the natural moisture barrier function of the epidermis and can be included in dry powder foundation described herein. Non-limiting examples of skin barrier repair actives include Alpha Lipid (available from Lucas Meyer); ascorbic acid; biotin; biotin esters; brassicasterol; caffeine; campesterol; canola derived sterols; Cennamides (available from Ennagram); Ceramax (available from Alban Muller); CERAMAX (available from Quest, located in Ashford, England); CERAMIDE 2 and CERAMIDE H03™ (both available from Sederma); CERAMIDE 11 (available from Quest); CERAMIDE III and IIIB (both available from Cosmoferm, located in Deft, Netherlands); CERAMIDE LS 3773 (available from Laboratories Serobiologiques); CERAMINOL (available from Inocosm); Cerasol and Cephalip (both available from Pentapharm); cholesterol; cholesterol hydroxystearate; cholesterol isostearate; 7 dehydrocholesterol; DERMATEIN BRC and DERMATEIN GSL (both available from Hormel); ELDEW CL 301 AND ELDEW PS 203 (both available from Ajinomoto); Fitobroside (available from Pentapharm); galactocerebrosides; Generol 122 (available from Henkel); glyceryl serine amide; hydroxyethyl isostearyl isopropanolamine; lactic acid; Lactomide (available from Pentapharm); lanolin; lanolin alcohols; lanosterol; lauric acid N laurylglucamide; lipoic acid; N-acetyl cysteine; N-acetyl-L-serine; N-methyl-L-Serine; Net Sterol-ISO (available from Barnet Products); vitamin $B_3$ compounds (such as niacinamide and nicotinic acid); palmitic acid; panthenol; panthetine; phosphodiesterase inhibitors; PHYTO/CER (available from Intergen); phytoglycolipid millet extract (available from Barnet Products Distributer, located in Englewood, N.J.); PHYTOSPHINGOSINE (available from Gist Brocades, located in King of Prussia, Pa.); PSENDOFILAGGRIN (available from Brooks Industries, located in South Plainfield, N.J.); QUESTAMIDE H (available from Quest); serine; sigmasterol; sitosterol; soybean derived sterols; sphingosine; sphingomylinase; S-lactoyl glutathione; stearic acid; Structurine (available from Silah); SUPER STEROL ESTERS (available from Croda); thioctic acid; THSC CERAMIDE OIL (available from Campo Research); trimethyl glycine; tocopheryl nicotinate; vitamin $D_3$; Y2 (available from Ocean Pharmaceutical); and mixtures thereof.

Non-Steroidal Cosmetic Soothing Actives

Cosmetic soothing actives can be effective in preventing or treating inflammation of the skin and can be included in the dry powder foundation described herein. The soothing active enhances the skin appearance benefits of the present invention, e.g., such agents contribute to a more uniform and acceptable skin tone or color.

The exact amount of anti-inflammatory agent to be used in the compositions will depend on the particular anti-inflammatory agent utilized since such agents vary widely in potency.

Non-limiting examples of cosmetic soothing agents include the following categories: propionic acid derivatives; acetic acid derivatives; fenamic acid derivatives; biphenylcarboxylic acid derivatives; and oxicams. All of these cosmetic soothing actives are fully described in U.S. Pat. No. 4,985,459 to Sunshine et al., issued Jan. 15, 1991, incorporated by reference herein in its entirety. Non-limiting examples of useful cosmetic soothing actives include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, bucloxic acid, absinthium, acacia, ACTIGEN Y (available from Active Organics), aescin, agrimony, alder buckthorn extract, allantoin, aloe, angelica, APT (available from Centerchem), arnica, astragalus, astragalus root extract, AVOCADIN HS-80 (available from Croda), avocado, azulene, Baicalin SR 15 (available from Barnet Products Dist.), baikal skullcap, baizhu, balm mint, balm of gilead, balsam canada, barley malt, basil, bayberry fruit, bee pollen, bladderwrack, BIODYNES TRF (available from Arch Personal Care), BIOPHYTEX (available from Laboratories Serobiologiques), bisabolol, black cohosh, black cohosh extract blue cohosh, blue cohosh extract, blue flag, boneset, borage, borage oil, bradykinin antagonists, bromelain, burdock root, butterbur, calendula, calendula extract, Canadian Willowbark Extract (available from Fytokem), candelilla wax, Cangzhu, canola phytosterols, capsicum, carboxypeptidase, celery seed, celery stem extract, CENTAURIUM (available from Sederma), centaury extract, chamazulene, chamomile, chamomile extract, chaparral, chaste tree, chaste tree extract, chickweed, chicory root, chicory root extract, chirata, chishao, collodial oatmeal, coltsfoot, comfrey, comfrey extract, coneflower, cornflower, CROMOIST CM GLUCAN (available from Croda), CYTOBIOL IRIS A (available from Gattefosse), darutoside, dehurian angelica, devil's claw, divalent metals (such as, magnesium, strontium, and manganese), doggrass, dogwood, dong quai, Eashave (available from Pentapharm), eleuthero, ELHIBIN (available from Pentapharm), ENTELINE 2 (available from Secma), ephedra, epimedium, esculoside; ethacrynic acid, evening primrose, eyebright, Extract LE-100 (available from Sino Lion), Fangfeng, fennel seed extract, feverfew, ficin, fir needle, forsythia fruit, Fytosterol 85 (available from Fytokem), ganoderma, gaoben, gardenia, Gatuline A (available from Gattefosse), gentian, germanium extract, gingko bilboa extract, ginkgo, ginseng extract, GIVOBIO GZn (available from Seppic), goldenseal, gorgonian extract, gotu kola, grape fruit extract, guaiac wood oil, guggal extract, helenalin esters, henna, honeysuckle flower, hops, horehound extract, horsechestnut, horsetail, huzhang, hypericum, Iceland moss, ichthyol, immortelle, ipecac, IRICALMIN (available from Pentapharm), irish moss, ivy, Japanese green tea, job's tears, jojoba, jujube, juniper berry, kava kava, kiwi, kola extract, kumquat, LANACHRYS 28 (available from Lana Tech), lemon oil, LEMON SECRETS (available from Gattefosse), lianqiao, licorice root, ligusticum, ligustrum, lime flower, linden, lovage root, luffa, mace, magnolia flower, mandarin orange, manjistha extract, margaspidin, marshmallow, matricin, meadowsweet, melatonin, MICROAT IRC (available from Nurture), mints, mistletoe, Modulene (available from Seporga), mono or diglucosides of glabridin, mono or diglucosides of gentisin, MTA (5'-deoxy-5'-methylhioadenosine), mulberry bark, mullein, mung bean extract, musk, myrrh, N-methyl arginine, nettle, neutral henna, oak bark, oat beta glucan, oat extract, orange, orange blossom, panthenol, papain, papaya, parsley, passion fruit, pear, periwinkle, pine cone, phenoxyacetic acid, peony bark, peony root, Phytoplenolin (available from Bio Botanica), phytosphingosine, plankton, Preregen (available from Pentapharm), prickly ash bark, purslane, QUENCH T (available from Centerchem), quillaia, red clover blossom, red sage, rehmannia, rhubarb, rice bran, roman chamomile, rose, rosemary, rosmarinic acid, royal jelly, rue, rutin, sandlewood, sanqi, sarsaparilla, saw palmetto, SENSILINE (available from Silab), SEPICALM S (available from Seppic), SEPICALM VG (available from Seppic), SIEGESBECKIA (available from Sederma), skullcap, slippery elm, soap bark, spearmint, SPHINGANINE (available from Croda), stearyl glycyrrhetinate, Stimutex (available from Pentapharm), storax, strontium nitrate, sweet birch oil, sweet woodniff, tagetes, tea extract, thyme extract, tienchi ginseng, tocopherol, tocopheryl acetate, triclosan, turmeric, urimei, ursolic acid, VEDACALM (available from Gattefosse), violet, white lily, white pine bark, wild cherry bark, witch hazel, yarrow, yeast extract, yucca, and mixtures thereof.

Skin Lightening Actives

Skin lightening actives can actually decrease the amount of melanin in the skin or provide such an effect by other mechanisms and can be included in the dry powder foundation described herein. Skin lightening actives suitable for use herein are described in co-pending patent application Ser. No. 08/479,935, filed on Jun. 7, 1995 in the name of Hillebrand, corresponding to International Patent Application No. PCT/US95/07432, filed Jun. 12, 1995; and copending patent application Ser. No. 08/390,152, filed on Feb. 24, 1995 and issued as U.S. Pat. No. 6,068,834 on May 30, 2000 in the names of Kalla L. Kvalnes, Mitchell A. DeLong, Barton J. Bradbury, Curtis B. Motley, and John D. Carter, corresponding to International Patent Application No. PCT/US95/02809, filed Mar. 1, 1995, published Sep. 8, 1995; all incorporated herein by reference.

Non-limiting examples of skin lightening actives useful herein include ACTIWHITE LS 9808 (available from Cognis), adapalene, almond extract, aloe extract, alpha-glycaryl-L-ascorbic acid, aminotyroxine, ammonium lactate, anethole derivatives, apple extract, arbutin, *areca catechu* L. extract, ascorbic acid, ascorbyl palmitate, azelaic acid, bamboo extract, bearberry extract, BELIDES (NP) (available from CLR Chemisches Laboratorium Dr. Kurt Richter GmbH), bletilla tuber, bupleurum falcatum extract, burnet extract, Burnet Power (available from Barnet Products), butyl hydroxy anisol, butyl hydroxy toluene, butyl resoreinol, Chuanxiong, cola decaballo extract, Dang-Gui, deoxyarbutin, DERMAWHITE NFLS 9410 (available from Cognis), 1,3 diphenyl propane derivatives, 2,5 dihydroxybenzoic acid and its derivatives, 2-(4-acetoxyphenyl)-1,3 dithane, 2-(4-hydroxyphenyl)-1,3 dithane, elder flower, ellagic acid, EMBILICA (available from EMD/Rona), escinol, estragole derivatives, esculoside, esculetin, ETIOLINE (available from Croda), FADEOUT (available from Pentapharm), Fangfeng, fennel extract, FISION SKIN LIGHT (available from Tri-K), gallic acid and its derivatives, ganodenna extract, gaoben, GATULINE WHITENING (available from Gattefosse), genistic acid and its derivatives, gentisyl alcohol, GIGAWHITE (available from Pentapharm), glabridin and its derivatives, gluco pyranosyl-1-ascorbate, gluconic acid, glucosamine, glycolic acid, glycyrrhizinic acid, green tea extract, horseradish, 4-Hydroxy-5-methyl-3 [2H]-furanone, hydroquinone, 4 hydroxyanisole and its derivatives, 4-hydroxy benzoic acid derivatives, hydroxycaprylic acid, hyptis extract, inositol ascorbate, kojic acid, kojic dipalmitate, lactic acid, lemon extract, licorice extract, Licorice P-TH (available from Barnet Products), linoleic acid, magnesium ascorbyl phosphate, MELACLEAR 2 (available from Croda), Melfade (available from Pentapharm), MELAWHITE (available from Pentapharm), Melanostatine DM (available from Laboratories Seporga), morus alba extract, mulberry root extract, NAB ASAFETIDA EXTRACT (available from Arch Personal Care), niacinamide, 5-octanoyl salicylic acid, papaya, parsley extract, phellinus linteus extract, pinon blanco extract, pinon negro extract, piri-piri extract, pyrogallol derivatives, retinoic acid, retinol, retinyl esters (acetate, propionate, palmitate, linoleate), 2,4 resorcinol derivatives, 3,5 resorcinol derivatives, rose fruit extract, rucinol, salicylic acid, SEPIWHITE MSH (available from Seppic), Song-Yi extract, Sophora Powder (available from Barnet Products), SYNERLIGHT (available from Gattefosse), 4-thioresorein, 3,4,5 trihydroxybenzyl derivatives, tranexamic acid, tyrostat (Rumex Extract available from Fytokem), Tyroslat 10,11 (available from Fytokem), VAMAWHITE GT (available from Tri-K), vanilla derivatives, vitamin D3 and its analogs, and mixtures thereof, WHITAMI (available from Alban Muller).

Sebum Stimulators

Sebum simulators can increase the production of sebum by the sebaceous glands and can be included in the dry powder foundation described herein. These skin care actives are especially useful for post menopausal women who are sebum deficient. Nonlimiting examples of sebum stimulating actives include bryonolic acid, completech MBAC-DS, dehydroetiandrosterone (also known as DHEA), orizanol and mixtures thereof.

Sebum Inhibitors

Sebum inhibitors can decrease the production of sebum by the sebaceous glands and can be included in the dry powder foundation described herein. Non-limiting examples of sebum inhibiting actives include AC.NET (available from Croda), ALMETH (available from Tri-K), aluminium hydroxy chloride, ASEBIOL (available from Laboratories Serobiologiques), BIODERMINE (available from Sederma), climbazole, COMPLETECH MBAC-OS (available from Lipo), corticosteroids, cucumber extracts, dehydroacetic acid and its salts, dichlorophenyl imidazoldioxolan (available from Elubiol), GIVOBIO GZn (available from Seppic), gugulipiu, ketoconazole, Lichochalcone LR 15 (available from Maruzen), niacinamide, phloretin, PHLOROGINE (available from Secma), Phycosaccharide Anti-Acne (available from Codif), PHYTOTAL OS (available from Croda), REGU-SEB (available from Pentapharm), S-carboxylmethyl cysteine, SEBORAMI (available from Alban Muller), SEPICONTROL AS (available from Seppic), spironolactone, tioxolone, tocopherol, tranexamic acid, LTNITRIENOL T27 (available from Unichem), INIREDUCE R_#% (available from Induchem USA), zincidone (UC1B), and mixtures thereof.

Protease Inhibitors

Also useful as active ingredients in the present invention are protease inhibitors.

Non-limiting examples of protease inhibitors which are useful in the compositions of the present invention are those selected from the group consisting of A E Complex (available from Barnet Products); ALE (available from Seporga); allicin; alpha lupaline; Aosaine (available from Secma); Aprotinin (available from Pentapharm); *areca catechu* (Betel Nut) extract; *areca catechu* extracts; Blue Algae Extract (available from Collaborative Labs); Centaurium (available from Sederma); cholesterol sulfate; CMST (available from Bioetica); Dermoprotectine (available from Sederma); Disacoside HF 60 (available from Barnet Products); Elhibin (available from Pentapharm); Fluid Out Colloid (available from Vegetech); Hypotaurine (available from Sogo Pharmaceutical); In Cyte Heathes (available from Collaborative Labs); Micromerol (available from Collaborative Labs); Pefabloc SP (available from Pentapharm); Sepicontrol AS (available from Seppic); Siegesbeckia (available from Sederma); Sophorine (available from Barnet Products); Thiotaine (available from Barnet Products); uncaria gambis roxburgh extract; zinc and mixtures thereof.

Skin Tightening Agents

Also useful as active ingredients in the present invention are skin tightening agents.

Non-limiting examples of skin tightening agents which are useful in the compositions of the present invention are those selected from the group consisting of Argatensyl LS 9735 (available from Cognis), Biocare SA (available from Amerchol); Easylift (available from Tri-K), egg albumen; Fision Skin Lift (available from Tri-K), Fision Soylift (available from Tri-K), Flexan 130 (available from National Starch); Gatuline Lifting (available from Gattefosse); Pentacare HP (available from Pentapharm); Pepha-Tight (available from Pentapharm), Quicklift (available from BASF), Sesaflash (available from Seppic), Skin Tightening ST (available from Croda), Soytensor LS 9811 (available from Cognis), Tritisol (available from Croda), Vegeseryl (available from Laboratories Serobioloques) and mixtures thereof.

Anti-Itch Ingredients

Also useful as active ingredients in the present invention are anti-itch ingredients.

Non-limiting examples of anti-itch ingredients which are useful in the compositions of the present invention are those selected from the group consisting of aloe vera, balm of gilead, beet, pennyroyal, peppermint, soapwort, Stimu-tex (available from Pentapharm); Takanal (available from Ikeda-Distributer); Ichthyol (available from International Sourcing-Distributor); Oxygenated Glyceryl Triesters (available from Seporgia) and mixtures thereof.

Antioxidants

Representative antioxidants include vitamin E, tocopheryl acetate, betaglucan, coenzyme Q10, butylated hydroxy toluene (BHT), butylated hydroxy anisole (BHA), superoxide dismutase, propylgallate, and the like.

II. Processing Method

The formulation described herein can be prepared by combining the various actives and excipients, and blending the resulting mixture. Particle size selection can be accomplished by screening, air stream segregation, and the like.

A flow agent is optionally added after the powder is manufactured. Flow agents which can be used in the present invention can be silica, clay, starch, and the like which can be added to the particles. Suitable fine silica materials are commercially available as pyrogenic or fumed silica, such as materials sold under Trade names of Cabosil manufactured by G. L. Cabot Inc., Aerogel 500 manufactured by J. M. Huber Corp., Syloid 244,-63,-65 manufactured by W. R. Grace and Co., Li-sil 233 manufactured by Pittsburg Plate Glass Co., and Sipernat D-17 manufactured by Degussa Co. Suitable clay materials include kaolinites and bentonites, as described in British Patent No. 1,460, 646.

The invention can be further illustrated by the following examples of preferred embodiments thereof, although it will be understood that these examples are included merely for purposes of illustration and are not intended to limit the scope of the invention unless otherwise specifically indicated. All percentages, ratios, and parts herein, in the Specification, Examples, and Claims, are by weight and are approximations unless otherwise stated.

Example 1

Safety and Efficacy Testing on Complete Formula

Three in-house studies with small sample sizes were conducted at Harmony Laboratories, Inc., to gather preliminary data relating to the safety and efficacy of the Acne Treatment Powder Foundation. In addition, subjective feedback regarding product aesthetics and performance was collected.

The formulations that were tested fell within the following composition:

TABLE 2

Summary of Acne Powder Sunscreen Foundation formulas developed and tested.

| Ingredient | Range % w/w |
|---|---|
| Iron Oxide, Bismuth Oxychloride & Mica blend | 48.75-68.75 |
| Titanium Dioxide | 8.10-35.00 |
| Zinc Oxide | 10.00-25.65 |
| Poly-Pore 450SA | 1.00 |
| Salicylic Acid & Allyl Methacrylates Crosspolymer | |
| ABS White Willow Bark Extract Powder | 2.00 |
| *Salix Nigra* (Willow) Bark Extract | |
| Phytocide Aspen Bark Extract Powder | 0.50 |
| *Populus Tremuloides* (Aspen) Bark Extract | |
| Givobio GZn | 1.00 |
| Zinc Gluconate | |
| Active Powder Purity LS 9695 | 0.25 |
| Exfoliance Bamboo | 0.50 |
| *Bambusa Arundinacea* Stem Powder | |
| PPP-100 Pearl Powder | 1.00 |
| Pearl Powder | |

Multiple formulas were tested, but each fell within the ranges listed above. Representative individual formulas are provided below in Examples 2-4.

Irritation Study—Volar Forearm

The first study assessed irritation resulting from product use and was evaluated on the volar forearm of study participants. Ten panelists, ages 20-55, with various skin types and complexions were selected to participate in this three day, baseline-controlled, randomized study. The powder foundation was applied to the same test site for three consecutive days, allowed to remain in place for 6 hours, and resulting irritation was compared to an untreated control site. Participants completed a sensory questionnaire immediately after and 6 hours after product application and were asked to comment on any adverse sensations, such as burning, itching or stinging. Furthermore, participants were asked to rate the degree of the reaction, ranging from 0 ("None") to 3.0 ("Severely Perceptible"). In addition to gathering sensory data, the study coordinator checked the control and test sites at baseline to confirm that both sites were clear. Six hours after product application the control and test sites were graded utilizing the following grading scale and letter grades.

Grading Scale

0=No Reaction
+=Slight, confluent or patchy erythema
1=Mild erythema (pink)
2=Moderate erythema (definite redness)
3=Strong erythema (very intense redness)

Letter Grades

E=Edema
P=Papule
V=Vesicle
B=Blister

TABLE 3

Percentage of Panelists with Visual Irritation

| Visual Signs of Irritation | Day 1 | Day 2 | Day 3 |
|---|---|---|---|
| 0 | 100% | 100% | 100% |
| + | 0% | 0% | 0% |

TABLE 3-continued

Percentage of Panelists with Visual Irritation

| Visual Signs of Irritation | Day 1 | Day 2 | Day 3 |
|---|---|---|---|
| 1 | 0% | 0% | 0% |
| 2 | 0% | 0% | 0% |
| 3 | 0% | 0% | 0% |
| E | 0% | 0% | 0% |
| P | 0% | 0% | 0% |
| V | 0% | 0% | 0% |
| B | 0% | 0% | 0% |

TABLE 4

Percentage of Panelists with Sensorial Irritation

| Sensorial Signs of Irritation | Day 1 | Day 2 | Day 3 |
|---|---|---|---|
| None | 100% | 100% | 100% |
| Burning | 0% | 0% | 0% |
| Itching | 0% | 0% | 0% |
| Stinging | 0% | 0% | 0% |
| Other | 0% | 0% | 0% |

Throughout the course of this in-house study, no panelist presented with irritation nor commented on any sensations relating to irritation. Furthermore, the Study Coordinator did not observe any visual signs of irritation at any time point during this three-day study.

Five Day Use Study—Face

The second small, in-house study was carried out to determine the product's ability to cause irritation in the form of visible changes and discomfort on facial skin. In addition, during the final day of the study, panelists completed a questionnaire to gather subjective feedback relating to product aesthetics and performance. Five women, ages 20-55, with normal to oily and oily skin types completed this baseline-controlled study. Each panelist was a user of loose powder foundation and agreed to substitute the test product in place of her usual foundation. Panelists had no known sensitivity to Salicylic Acid and for the duration of the study, as well as one week prior to the study, panelists were not allowed to use any additional facial products with Salicylic Acid or Benzoyl Peroxide, nor any abrasive cleansers or scrubs. Furthermore, panelists were not current users of Retin-A or any other topical acne prescription treatments. Finally, all panelists were free of any active dermatitis and had no recent sunburn on the facial skin.

Each morning during the study, the panelist followed her usual cleansing and moisturizing routine, applied the test product with an applicator brush provided, and followed with application of her usual color cosmetic products. Following application, the panelist completed a questionnaire to gather any sensorial data relating to irritation (i.e. burning, itching, stinging, and the like.). The loose powder foundation was worn for a minimum of eight hours each day and then removed with panelist's usual cleansing products. Prior to removal, panelists completed the same sensorial questionnaire to comment on any irritation experienced during the day. Finally, on the fifth and final day of the study, the panelists completed self-assessment questionnaires to offer subjective data. Throughout the duration of the study, panelists were observed by the Study Coordinator and checked for any signs of irritation.

TABLE 5

Percentage of Panelists with Irritation

| Sensorial Signs of Irritation | Day 1 | Day 2 | Day 3 | Day 4 | Day 5 |
|---|---|---|---|---|---|
| None | 100% | 100% | 100% | 100% | 100% |
| Burning | 0% | 0% | 0% | 0% | 0% |
| Itching | 0% | 0% | 0% | 0% | 0% |
| Stinging | 0% | 0% | 0% | 0% | 0% |
| Other | 0% | 0% | 0% | 0% | 0% |

TABLE 6

Subjective Feedback on Product Performance

| Comments | Day 1 |
|---|---|
| Less Blemishes/Clearer Complexion | 40% |
| Good Coverage | 80% |
| Better Coverage than Current Powder Foundation | 40% |
| Better Oil Control than Current Loose Powder Foundation | 60% |

Following five days of product use, none of the panelists experienced any irritation, either visual or sensorial. Sixty percent of panelists felt the product offered better oil control compared to their current powder foundation, while 40% saw less blemishes or a clearer complexion during the study. Eighty percent felt the powder offered good coverage, while 40% felt it offered better coverage than their usual powder foundation. Additional feedback from study participants related to the powder's light feel, long wearability, and brightening effect on the skin.

Study to Assess Changes in Surface Sebum Levels—Forehead

The third, in-house study was carried out to determine the powder foundation's ability to control surface sebum levels on the forehead. Sebum, which is composed of triglycerides, diglycerides, free fatty acids, wax esters, squalene, cholesterol, and cholesterol esters, is produced by the sebaceous glands to keep the skin and hair moisturized. It is responsible for giving the skin an oily appearance, and its removal is an important performance characteristic in many skin care and cosmetic products. Excess sebum, which is exacerbated by high humidity conditions, can make the skin resistant to makeup application, as well as lead to comedone formation.

Seven women, ages 20-55, with normal to oily and oily skin types completed this one-day, baseline-controlled study. Panelists had no known sensitivity to Salicylic Acid nor were current users of products containing Salicylic Acid, Benzoyl Peroxide, or any type of prescription medications containing retinoic acid, such as Retin-A. Study participants also had to be free of any irritation on the forehead and could not have any recent sunburn on the forehead. For the duration of the study, bangs had to be secured away from the face and forehead.

In this clinical study, the test product was applied to three test sites on the forehead, and each test site had a corresponding untreated, control site. At various time points during this 6 hour study, one test site and its corresponding control site were evaluated for sebum output using SEBUTAPE® Skin Indicators (CuDerm Corporation, Dallas, Tex.). SEBUTAPE® is designed to assess sebum output and distribution of active sebaceous glands. It is made of a microporous, hydrophobic film with numerous air cavities. Once the tape is applied to the skin, sebum displaces air in the cavities and is absorbed onto the tape. Sebum output from each follicle will form a clearly defined spot and can be assessed visually for a crude measure of follicle activity and sebum volume.

Panelists meeting the study criteria were checked at baseline to ensure that the forehead area was free of any irritation. The entire forehead was cleansed with Dove Soap to remove makeup, sebum, or additional debris, and the area was patted dry with gauze. Six total test sites (3 control and 3 test) were identified across the forehead using the study template, composed of 6 test sites each measuring approximately 1.5 cm$^2$. The order of the test sites across the forehead was randomized among the panel. To the three test sites, approximately 0.02 g of product was applied using a sponge-tipped applicator and rubbed gently and evenly on the skin for 5 seconds. One control and one test site were measured with SEBUTAPE® at 1, 3, and 6 hours post product application. The skin indicators were applied to the control and, test sites for a total of 5 seconds and removed. Care was taken to apply the same degree of pressure when sebum samples were gathered. Surface sebum levels of the control and test sites were visually assessed following the enclosed instructions and grading scale:

Grading Scale

L=Low
M=Medium
H=High

TABLE 7

Percentage of Panelists with Changes in Surface Sebum Levels

|  | 1 Hour post product application | 3 Hours post product application | 6 Hours post product application |
|---|---|---|---|
| No Change | 43%* | 43%** | 29% |
| Reduction | 57% | 57% | 71% |
| Increase | 0% | 0% | 0% |

*100% of these panelists were classified as L. Thus, no improvement could be indicated according to the grading scale.
**67% of these panelists were classified as L.

TABLE 8

Percentage of Panelists with Reduction in Surface Sebum Levels - Improvement by Degree of Oiliness

|  | 1 Hour post product application | 3 Hours post product application | 6 Hours post product application |
|---|---|---|---|
| L | — | — | — |
| M | 100% | 100% | 75% |
| H | 100% | 50% | 67% |

The results show that all panelists experienced a reduction in sebum output at least at 1 time point during this 6-hour study. One and three hours post product application, 57% of panelists experienced an improvement in sebum output, while 71% showed improvements at the 6 hour time point. One hundred percent of those panelists with medium and high levels of sebum showed a reduction at the one-hour time point. At the three-hour time point, those with a medium level of sebum output showed the same improvement, while 50% of those with a high level improved. Six hours post product application, 75% of those with a medium level and 67% with a high level showed a reduction in surface sebum output. At the one and three-hour time points, 5 participants were classified as having a low level of sebum output, and thus, there was no way to visually assess any improvements based on the visual scale provided by CuDerm. Finally, no participant showed a greater degree of sebum output with the test product in place compared to the corresponding, untreated control site.

Summary:

While there are a variety of loose powder foundations on the market, most are promoted based solely on their cosmetic attributes, such as coverage and wearability. Addition of ingredients to help treat the acne condition and provide sun protection extends this product type past that of a mere cosmetic. Acne Treatment Powder Foundation with SPF 15 combats acne by reducing & regulating sebum production, providing gentle exfoliation, fighting *P. acnes* and other harmful microbes, soothing irritation and inflammation, and restoring barrier function.

Clinical testing carried out on the individual raw materials selected for this product demonstrated their effectiveness at combating various aspects contributing to the acne condition, such as overproduction of sebum and *P. acnes* overgrowth. Furthermore, in-house studies conducted at HLI preliminarily confirm that the product is non-irritating, controls surface sebum levels, and provides good coverage and long wearability.

Examples 2-4

Representative Formulations: Powder Shades Evaluated During in-House Studies

In the Irritation Study (Volar Forearm) described above, there was one shade tested in this study. The formulation is provided below.

| Ingredient | Range % w/w |
|---|---|
| Iron Oxide, Bismuth Oxychloride & Mica blend | 54.25 |
| Titanium Dioxide | 17.50 |
| Zinc Oxide | 22.00 |
| Poly-Pore 450SA | 1.00 |
| Salicylic Acid & Allyl Methacrylates Crosspolymer | |
| ABS White Willow Bark Extract Powder | 2.00 |
| *Salix Nigra* (Willow) Bark Extract | |
| Phytocide Aspen Bark Extract Powder | 0.50 |
| *Populus Tremuloides* (Aspen) Bark Extract | |
| Givobio GZn | 1.00 |
| Zinc Gluconate | |
| Active Powder Purity LS 9695 | 0.25 |
| Exfoliance Bamboo | 0.50 |
| *Bambusa Arundinacea* Stem Powder | |
| PPP-100 Pearl Powder | 1.00 |
| Pearl Powder | |

For the Five Day Use Study—Face, there were three shades tested in this study. The amount of iron oxide, bismuth oxychloride, mica blend, titanium dioxide, and zinc oxide varied depending on the shade. The following table shows the variations in these formulations.

| Ingredient | Range % w/w |
|---|---|
| Iron Oxide, Bismuth Oxychloride & Mica blend | 48.75-60.00 |
| Titanium Dioxide | 8.10-35.00 |
| Zinc Oxide | 10.00-25.65 |
| Poly-Pore 450SA | 1.00 |
| Salicylic Acid & Allyl Methacrylates Crosspolymer | |
| ABS White Willow Bark Extract Powder | 2.00 |
| *Salix Nigra* (Willow) Bark Extract | |

-continued

| Ingredient | Range % w/w |
|---|---|
| Phytocide Aspen Bark Extract Powder<br>*Populus Tremuloides* (Aspen) Bark Extract | 0.50 |
| Givobio GZn<br>Zinc Gluconate | 1.00 |
| Active Powder Purity LS 9695 | 0.25 |
| Exfoliance Bamboo<br>*Bambusa Arundinacea* Stem Powder | 0.50 |
| PPP-100 Pearl Powder<br>Pearl Powder | 1.00 |

In the Study to Assess Changes in Surface Sebum Levels—Forehead, there were two shades tested in this study. The amount of iron oxide, bismuth oxychloride, mica blend, titanium dioxide, and zinc oxide varied depending on the shade. The following table shows the variations in these formulations.

| Ingredient | Range % w/w |
|---|---|
| Iron Oxide, Bismuth Oxychloride & Mica blend | 54.25-68.75 |
| Titanium Dioxide | 10.00-17.50 |
| Zinc Oxide | 15.00-22.00 |
| Poly-Pore 450SA<br>Salicylic Acid & Allyl Methacrylates Crosspolymer | 1.00 |
| ABS White Willow Bark Extract Powder<br>*Salix Nigra* (Willow) Bark Extract | 2.00 |
| Phytocide Aspen Bark Extract Powder<br>*Populus Tremuloides* (Aspen) Bark Extract | 0.50 |
| Givobio GZn<br>Zinc Gluconate | 1.00 |
| Active Powder Purity LS 9695 | 0.25 |
| Exfoliance Bamboo<br>*Bambusa Arundinacea* Stem Powder | 0.50 |
| PPP-100 Pearl Powder<br>Pearl Powder | 1.00 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A foundation for skin care, comprising:
   a) a sustained-release salicylic acid formulation,
   b) one or more salicylate salts in powder form in contact with the sustained-release salicylic acid formulation in an effective, buffering amount which at least partially neutralizes the acidic nature of the salicylic acid,
   c) zinc oxide,
   d) titanium dioxide, and
   e) two or more components selected from the group consisting of zinc gluconate, horse chestnut seed extract, pearl powder, and bamboo extract,
   wherein the foundation is in the form of a dry powder, and wherein the salicylate salts are selected from the group consisting of extracts of white willow bark, extracts of aspen bark, ammonium salicylate, sodium salicylate, potassium salicylate, magnesium salicylate, calcium salicylate, strontium salicylate, barium salicylate, aluminum salicylate, iron salicylate, zinc salicylate, bismuth salicylate and salts formed between salicylic acid and organic amines.

2. The foundation of claim 1, wherein one of the two or more components selected from the group consisting of zinc gluconate, horse chestnut seed extract, pearl powder, and bamboo extract is zinc gluconate.

3. The foundation of claim 1, wherein one of the two or more components selected from the group consisting of zinc gluconate, horse chestnut seed extract, pearl powder, and bamboo extract is horse chestnut seed extract.

4. The foundation of claim 1, wherein one of the two or more components selected from the group consisting of zinc gluconate, horse chestnut seed extract, pearl powder, and bamboo extract is pearl powder.

5. The foundation of claim 1, wherein one of the two or more components selected from the group consisting of zinc gluconate, horse chestnut seed extract, pearl powder, and bamboo extract is bamboo extract.

6. The foundation of claim 1, further comprising one or more pigments or colorants.

7. The foundation of claim 1, wherein the pigment or colorant comprises one or more of iron oxide, bismuth oxychloride, and mica.

8. The foundation of claim 1, further comprising a UV absorber.

9. The foundation of claim 1, wherein the UV absorber is 3-benzophenone or avobenzone.

10. The foundation of claim 1, wherein the salicylate salts are extracts of white willow bark or extracts of aspen bark.

11. The foundation of claim 1, wherein the amount of zinc oxide ranges between about 5 and about 35 weight percent.

12. The foundation of claim 1, wherein the range of salicylic acid sustained release composition is 0.1-12.0% by weight of the composition.

13. The foundation of claim 1, wherein the salicylate salts are extracts of white willow bark or extracts of aspen bark, and the amount of the extracts is 0.1-10.0% by weight of the composition.

14. The foundation of claim 1, further comprising one or more colorants or pigments, wherein the range of said colorants or pigments is 40-75% by weight of the composition.

15. The formulation of claim 1, further comprising one or more additional anti acne agents, selected from the group consisting of sulfur, benzoyl peroxide, resorcinol, and resorcinol monoacetate.

16. The foundation of claim 1, wherein the amount of titanium dioxide is between about 5 and about 40 weight percent.

17. The foundation of claim 1, wherein the formulation comprises at least 10% of the molar amount of salicylates, relative to salicylic acid.

18. The foundation of claim 1, wherein the salicylate salts are extracts of white willow bark or extracts of aspen bark, and the amount of the extracts is 0.1-10.0% by weight of the composition and wherein the range of salicylic acid sustained release composition is 0.1-12.0% by weight of the composition.

19. The foundation of claim 1, wherein the salicylic acid and the one or more salicylate salts are each in concentrations from about 0.05% to about 12.0% by weight, wherein the amount of free salicylic acid is from about 0.1 to about 6.0% by weight.

* * * * *

UNITED STATES PATENT AND TRADEMARK OFFICE
CERTIFICATE OF CORRECTION

PATENT NO. : 9,125,919 B2
APPLICATION NO. : 12/639851
DATED : September 8, 2015
INVENTOR(S) : John D. Maloney et al.

It is certified that error appears in the above-identified patent and that said Letters Patent is hereby corrected as shown below:

In the specification,

Column 12, lines 58-59: "(esters of $C_{2.20}$ alcohols);"
should be -- "(esters of $C_{2-20}$ alcohols);" --.

In the claims,

Column 24, Claim 9, lines 25-26:
"9. The foundation of claim 1, wherein the UV absorber is 3-benzophenone or avobenzone."
should be
-- 9. The foundation of claim 8, wherein the UV absorber is 3-benzophenone or avobenzone. --.

Column 24, Claim 15, lines 42-44:
"15. The formulation of claim 1, further comprising one or more additional anti acne agents, selected from the group consisting of sulfur, benzoyl peroxide, resorcinol, and resorcinol monoacetate."
should be
-- 15. The foundation of claim 1, further comprising one or more additional anti acne agents, selected from the group consisting of sulfur, benzoyl peroxide, resorcinol, and resorcinol monoacetate. --.

Signed and Sealed this
First Day of December, 2015

Michelle K. Lee
*Director of the United States Patent and Trademark Office*